United States Patent
O'Phelan et al.

(10) Patent No.: US 6,385,490 B1
(45) Date of Patent: May 7, 2002

(54) CAPACITORS WITH RECESSED RIVETS ALLOW SMALLER IMPLANTABLE DEFIBRILLATORS

(75) Inventors: Michael J. O'Phelan, Oakdale, MN (US); Robert R. Tong, Folsom, CA (US); Luke J. Christenson, White Bear Lake, MN (US); Steven A. Rubin, Sharon, MA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/607,382

(22) Filed: Jun. 30, 2000

Related U.S. Application Data

(63) Continuation of application No. 09/465,095, filed on Dec. 16, 1999, now abandoned.

(51) Int. Cl.[7] ............................................. A61N 1/38
(52) U.S. Cl. .......................... 607/5; 607/36; 361/537
(58) Field of Search ............................ 607/4, 5, 9, 119, 607/36; 361/302, 509, 520, 537

(56) References Cited

U.S. PATENT DOCUMENTS

| | | | |
|---|---|---|---|
| 3,398,333 A | 8/1968 | Zeppieri | 317/230 |
| 3,555,369 A | 1/1971 | Yoshino et al. | 317/230 |
| 3,659,615 A | 5/1972 | Enger | 128/419 P |
| 3,765,956 A | 10/1973 | Li | 148/33 |
| 3,789,502 A | 2/1974 | Callins et al. | 29/570 |
| 3,918,460 A | 11/1975 | King et al. | 128/419 P |

(List continued on next page.)

FOREIGN PATENT DOCUMENTS

| | | | |
|---|---|---|---|
| EP | 0753868 | 1/1997 | H01G/9/012 |
| EP | 0851446 | 7/1998 | H01G/9/055 |
| WO | 99/51301 | 10/1999 | A61N/1/375 |
| WO | 99/51302 | 10/1999 | A61N/1/375 |
| WO | 99/51303 | 10/1999 | A61N/1/39 |
| WO | 99/66985 | 12/1999 | A61N/1/39 |

OTHER PUBLICATIONS

Database WPI Abstract XP–002126511, An–1997–031410 (03), Publication No. JP 08293430, Derwent Publications Ltd., London GB, 1 p., (Nov. 5, 1996).
Patent Abstracts of Japan, 15 (40), Publication No. 02276222 (U. Noriki), 1 p., (Nov. 13, 1990).
Patent Abstracts of Japan, 16 (134), Publication No. 03296207 (K. Kaname), 1 p., (Dec. 26, 1991).
Patent Abstracts of Japan, 16 (291), Publication No. 04074409 (A. Akiyoshi), p., (Jul. 16, 1990).

(List continued on next page.)

*Primary Examiner*—Jeffrey R. Jastrzab
*Assistant Examiner*—Frances P. Oropeza
(74) *Attorney, Agent, or Firm*—Schwegman, Lundberg, Woessner & Kluth, P.A.; Eduardo E. Drake

(57) ABSTRACT

Implantable defibrillators are implanted into the chests of patients prone to suffering ventricular fibrillation, a potentially fatal heart condition. Critical components in these devices are aluminum electrolytic capacitors, which store and deliver one or more life-saving bursts of electric charge to a fibrillating heart. These capacitors make up about one third the total size of the defibrillators. Unfortunately, manufacturers of these capacitors have paid little or no attention to reducing the size of these capacitors through improved capacitor packaging. Accordingly, the inventors devised a unique capacitor lid, or header, assembly that allows size reduction. Specifically, one embodiment of the header assembly includes two recesses, each with a depth that allows the head of a rivet (or other fastener) to be substantially flush, or coplanar, with the underside of the header. Another embodiment includes a single recess to receive two rivet heads. The recesses reduce the vertical space necessary to ensure separation of the rivets from internal components of the capacitor and thus allow reduction in the overall height of the capacitor and size of devices, such as implantable defibrillators, that use them.

14 Claims, 4 Drawing Sheets

U.S. PATENT DOCUMENTS

| | | | |
|---|---|---|---|
| 3,943,937 A | 3/1976 | King et al. | 128/419 P |
| 4,041,955 A | 8/1977 | Kelly et al. | 128/419 P |
| 4,041,956 A | 8/1977 | Purdy et al. | 128/419 P |
| 4,136,435 A | 1/1979 | Li | 29/572 |
| 4,183,600 A | 1/1980 | Schroeder | 339/218 R |
| 4,243,042 A | 1/1981 | Ware | 128/419 P |
| 4,333,469 A | 6/1982 | Jeffcoat et al. | 128/419 F |
| 4,371,406 A | 2/1983 | Li | 148/171 |
| 4,385,342 A | 5/1983 | Puppolo et al. | 361/433 |
| 4,395,305 A | 7/1983 | Whitman | 156/665 |
| 4,521,830 A | 6/1985 | Aultman et al. | 361/433 |
| 4,546,415 A | 10/1985 | Kent et al. | 361/433 |
| 4,663,824 A | 5/1987 | Kenmochi | 29/570 |
| 4,690,714 A | 9/1987 | Li | 437/208 |
| 4,692,147 A | 9/1987 | Duggan | 604/93 |
| 4,771,362 A | 9/1988 | Behn | 361/306 |
| 4,782,235 A | 11/1988 | Lejeune et al. | 250/423 R |
| 4,907,130 A | 3/1990 | Boulloy et al. | 361/529 |
| 4,942,501 A | 7/1990 | MacFarlane et al. | 361/523 |
| 4,944,300 A | 7/1990 | Saksena | 128/419 D |
| 4,987,519 A | 1/1991 | Hutchins et al. | 361/518 |
| 5,055,889 A | 10/1991 | Beall | 357/14 |
| 5,055,975 A | 10/1991 | Behrend | 361/527 |
| 5,086,374 A | 2/1992 | MacFarlane et al. | 361/525 |
| 5,131,388 A | 7/1992 | Pless et al. | 128/419 D |
| 5,146,391 A | 9/1992 | MacFarlane et al. | 361/525 |
| 5,153,820 A | 10/1992 | MacFarlane et al. | 361/525 |
| 5,245,499 A | 9/1993 | Senes | 361/56 |
| 5,275,621 A | 1/1994 | Mehra | 607/5 |
| 5,324,910 A | 6/1994 | Isawa | 219/118 |
| 5,370,663 A | 12/1994 | Lin | 607/5 |
| 5,380,341 A | 1/1995 | Matthews et al. | 29/25.03 |
| 5,439,760 A | 8/1995 | Howard et al. | 429/94 |
| 5,456,698 A | 10/1995 | Byland et al. | 607/36 |
| 5,468,984 A | 11/1995 | Efland et al. | 257/356 |
| 5,500,534 A | 3/1996 | Robinson et al. | 250/385.1 |
| 5,522,851 A | 6/1996 | Fayram | 607/5 |
| 5,536,960 A | 7/1996 | Hayashi | 257/369 |
| 5,536,964 A | 7/1996 | Green et al. | 257/432 |
| 5,545,184 A | 8/1996 | Dougherty | 607/5 |
| 5,584,890 A | 12/1996 | MacFarlane et al. | 29/25.03 |
| 5,591,211 A | 1/1997 | Meltzer | 607/5 |
| 5,597,658 A | 1/1997 | Kejha | 429/94 |
| 5,628,801 A | 5/1997 | MacFarlane et al. | 29/25.03 |
| 5,642,252 A | 6/1997 | Sakamoto et al. | 361/93 |
| 5,660,737 A | 8/1997 | Elias et al. | 216/6 |
| 5,661,625 A | 8/1997 | Yang | 361/92 |
| 5,661,629 A | 8/1997 | MacFarlane et al. | 361/505 |
| 5,674,260 A | 10/1997 | Weinberg | 607/36 |
| 5,677,539 A | 10/1997 | Apotovsky et al. | 250/370.13 |
| 5,679,033 A * | 10/1997 | Eavey et al. | 439/801 |
| 5,688,698 A | 11/1997 | Robinson et al. | 437/3 |
| 5,697,953 A | 12/1997 | Kroll et al. | 607/5 |
| 5,698,453 A | 12/1997 | Green et al. | 437/3 |
| 5,711,861 A | 1/1998 | Ward et al. | 204/403 |
| 5,711,988 A | 1/1998 | Tsai et al. | 427/80 |
| 5,728,594 A | 3/1998 | Efland et al. | 437/40 |
| 5,748,439 A | 5/1998 | MacFarlane et al. | 361/525 |
| 5,776,628 A | 7/1998 | Kraft et al. | 429/94 |
| 5,800,857 A | 9/1998 | Ahmad et al. | 427/80 |
| 5,808,857 A | 9/1998 | Stevens | 361/503 |
| 5,814,082 A | 9/1998 | Fayram et al. | 607/5 |
| 5,837,995 A | 11/1998 | Chow et al. | 250/214 LS |
| 5,859,456 A | 1/1999 | Efland et al. | 257/335 |
| 5,867,363 A | 2/1999 | Tsai et al. | 361/502 |
| 5,895,416 A | 4/1999 | Barreras, Sr. et al. | 607/62 |
| 5,895,733 A | 4/1999 | Crespi et al. | 429/219 |
| 5,904,514 A | 5/1999 | Konuma et al. | 438/165 |
| 5,908,151 A * | 6/1999 | Elias | 228/110.1 |
| 5,926,357 A | 7/1999 | Elias et al. | 361/302 |
| 5,930,109 A | 7/1999 | Fishler | 361/508 |
| 5,949,638 A | 9/1999 | Greenwood, Jr. et al. | 361/508 |
| 5,959,535 A | 9/1999 | Remsburg | 340/604 |
| 5,963,418 A | 10/1999 | Greenwood, Jr. et al. | 361/508 |
| 5,968,210 A | 10/1999 | Strange et al. | 29/25.03 |
| 5,980,977 A | 11/1999 | Deng et al. | 427/79 |
| 5,983,472 A | 11/1999 | Fayram et al. | 29/25.42 |
| 6,006,133 A | 12/1999 | Lessar et al. | 607/5 |
| 6,009,348 A | 12/1999 | Rorvick et al. | 607/5 |

OTHER PUBLICATIONS

Patent Abstracts of Japan, 18 (3), Publication No. 05251283 (T. Fumiyasu), 1 p., (Sep. 28, 1993).

Patent Abstracts of Japan, 1996 (6), Publication No. 08055762 (E. Akira), 1 p., (Feb. 27, 1996).

Patent Abstracts of Japan, 97 (12), Publication No. 09219343 (I. Toshihiko), 1 p., (Aug. 19, 1997).

"Understanding Aluminum Electrolytic Capacitors", *United Chemi–Con,* 7 p., (Date Unknown).

Jenkins, et al., "Diagnosis of Atrial Fibrillation Using Electrogram from Chronic Leads: Evaluation of Computer Algorithm", *PACE,* 11, pp. 622–632, (1988).

Lunsman, P., et al., "High–Energy Density Capacitors for Implantable Defibrillators", *Proceedings of the 16th Capacitor and Resistor Technology Symposium,* Monteleone Hotel, New Orleans, Louisiana, pp. 277–280, (Mar. 11–15, 1996).

Morris, et al., "Intracardiac Electrogram Transformation: Morphometric Implications for Implantable Devices", *Journal of Electrocardiology,* 29 Supplement, pp. 124–129 (1996).

Moynihan, J.D., et al., "Theory, Design and Application of Electrolytic Capacitors", Copyright by John D. Moynihan, 136 p., (1982).

Schuller, et al., "Far Field R–Wave Sensing—An Old Problem Repeating", *PACE,* 19, Part II, NASPE Abstract No. 264, p. 631 (1996).

Stephany, et al., "Real–Time Estimation of Magnitude–Square Coherence for Use in Implantable Devices", *IEEE Computers in Cardiology,* pp. 375–378 (1992).

* cited by examiner

CAPACITORS WITH RECESSED RIVETS ALLOW SMALLER IMPLANTABLE DEFIBRILLATORS

CROSS REFERENCE TO RELATED APPLICATIONS

This application is a continuation of U.S. patent application Ser. No. 09/465,095, filed on Dec. 16, 1999, the specification of which is incorporated herein by reference now abandoned.

BACKGROUND OF THE INVENTION

The present invention concerns capacitors, particularly those for use in medical devices, such as implantable defibrillators.

Every year more than half a million people in the United States suffer from heart attacks, more precisely cardiac arrests. Many of these cardiac arrests stem from the heart chaotically twitching, or fibrillating, and thus failing to rhythmically expand and contract as necessary to pump blood. Fibrillation can cause complete loss of cardiac function and death within minutes. To restore normal heart contraction and expansion, paramedics and other medical workers use a device, called a defibrillator, to electrically shock a fibrillating heart.

Since the early 1980s, thousands of patients prone to fibrillation episodes have had miniature defibrillators implanted in their bodies, typically in the left breast region above the heart. These implantable defibrillators detect onset of fibrillation and automatically shock the heart, restoring normal heart function without human intervention. The typical implantable defibrillator includes a set of electrical leads, which extend from a sealed housing into the heart of a patient after implantation. Within the housing are a battery for supplying power, heart-monitoring circuitry for detecting fibrillation, and a capacitor for storing and delivering a burst of electric charge through the leads to the heart.

The capacitor is typically an aluminum electrolytic capacitor. This type of capacitor usually includes stacked strips of aluminum foil and paper rolled up to form a cylindrical structure called an active element. The active element is typically placed in a round tubular can which is sealed shut with a flat circular lid, known as a header. (The header usually consists of two thin bonded layers, one rubber and the other phenolic resin.) Extending from the header are two terminals connected to the rolled up foils in the active element. The terminals are usually fastened to the lid using two rivets.

Each rivet has a short shank, or rod, with a broad head on one end. (The rivet head, typically round like the head of a nail, has a diameter of about four millimeters (three sixteenths of an inch) and a thickness of about one millimeter.) The shank extends through holes in the terminal and the header, with the head resting against the interior side of the header and its opposite end extending from the exterior side. The opposite end is flattened or otherwise deformed to prevent the shank from passing back through its hole, thereby fastening the terminal to the header.

In recent years, manufacturers of electrolytic capacitors have focused almost single-mindedly on improving the active element by developing aluminum foils, electrolytes, and multiple-anode arrangements that improve capacitor performance, specifically energy density—the amount of energy or charge a capacitor stores per unit volume. For example, because energy density is directly proportional to the surface area of the aluminum foil making up the active element, manufacturers have developed methods of etching microscopic hills and valleys into foil to increase its effective surface area.

In comparison, capacitor manufacturers have made little or no effort to reduce the size of capacitors through space-saving assembly techniques. For example, the inventors determined that the conventional use of rivets to fasten terminals to the capacitor lid, or header, wastes space. Specifically, they determined that conventional capacitor manufacturers generally increase capacitor height (or reduce foil dimensions) to accommodate the heads of the rivets that fasten terminals to headers. The rivet heads are electrically conductive and must be prevented from touching, or contacting, the foils in the active element. So, capacitor manufacturers increase the height of the case to provide clearance between the rivet heads and the foils. Unfortunately, this increases not only the size of the capacitors, but also the size of devices, such as implantable defibrillators, that incorporate them.

Accordingly, the inventors identified an unmet need to reduce the size of electrolytic capacitors, especially those intended for implantable defibrillators, through better techniques and structures for fastening terminals to capacitor headers.

SUMMARY OF THE INVENTION

To address this and other needs, the inventors devised a capacitor having a header which includes one or more recesses. The recess receives the head of a rivet or other fastener and thus reduces or eliminates the need to increase capacitor height or reduce foil dimensions to achieve clearance between the fasteners and other capacitor parts, such as active-element foils. More particularly, the exemplary embodiment includes a header having two recesses, each with a depth that allows the head of a rivet to be substantially flush, or coplanar, with the underside of the header. In another embodiment, the header has a single recess to receive two rivet heads.

In devising this improvement, the inventors departed from at least two conventional capacitor design objectives: reducing the number of assembly steps per capacitor and reducing manufacturing waste or cost. Conventional capacitor manufacturers make hundreds of thousands or even millions of capacitors every year and are thus continually seeking ways to reduce capacitor assembly time. Indeed, saving (that is, omitting or skipping) even one manufacturing step amounts to considerable time and cost savings when multiplied by hundreds of thousands or millions of capacitors. Conversely, adding a step, such as forming one or more recesses in a header, to the manufacture of each capacitor generally increases assembly time and cost.

Similarly, conventional capacitor manufacturers who make thousands or millions of capacitors may also be concerned about reducing material waste, particularly seeking and developing capacitor designs and assembly practices which minimize or reduce the risk of destroying an entire capacitor or capacitor part during manufacture. Indeed, designs and manufacturing steps which pose a high risk of destroying an entire capacitor or capacitor part, such as a header, are generally avoided. Conventional headers are only about 2.5 millimeters thick and comprise two bonded layers of material. Forming one or more recesses in this type header not only adds a step to the manufacturing process, but also presents a risk of destroying it and thus increasing manufacturing waste and cost.

BRIEF DESCRIPTION OF THE DRAWINGS

FIG. 2 is a cross-sectional view of capacitor 10 in FIG. 1 taken along line 2—2 to show internal details of the capacitor, including an exemplary header assembly 14 having a recess 14c which receives a rivet head 17a.

FIG. 3 is a top perspective view of a header assembly 14 which comprises a recess 16 for the heads of rivets 15a and 17a.

DESCRIPTION OF THE PREFERRED EMBODIMENTS

The following detailed description, which references and incorporates FIGS. 1–6, describes and illustrates one or more specific embodiments of the invention. These embodiments, offered not to limit but only to exemplify and teach, are shown and described in sufficient detail to enable those skilled in the art to implement or practice the invention. Thus, where appropriate to avoid obscuring the invention, the description may omit certain information known to those of skill in the art.

Figure 1:
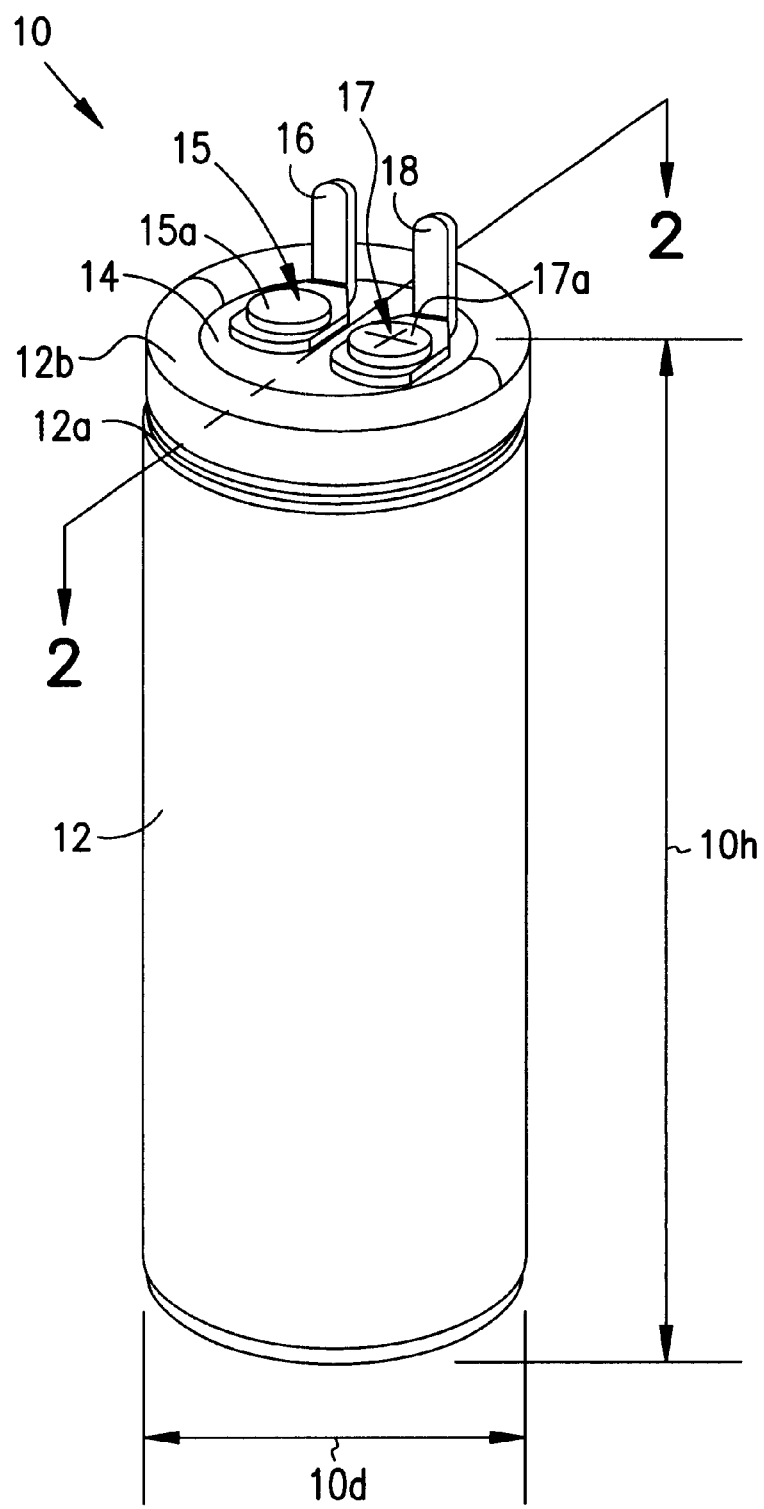
FIG. 1 is a perspective view of an exemplary cylindrical electrolytic capacitor 10 embodying the present invention.

FIG. 1 shows a perspective view of an exemplary electrolytic capacitor 10 which incorporates a space-saving header assembly according to the present invention. Capacitor 10, which has a height 10h and a diameter 10d, includes a cylindrical aluminum case, a header (or lid) assembly 14, and two electrically conductive terminals 16 and 18. (Height 10h is measured along a longitudinal axis.) Two aluminum rivets 15 and 17 respectively fasten terminals 16 and 18, which for example comprise solid aluminum or steel with a solder plate, to header assembly 14. Rivets 15 and 17 include respective upper heads 15a and 17a, and respective lower heads 15b and 17b, which are joined via respective intermediate rods, or shanks, 15c and 17c. (Lower heads 15b and 17b and shank 15c and 17c are visible in this perspective view. With the exception of shank 15c, which is not visible in any of the Figures, shank 17c and heads 15b and 17b are shown respectively in FIG. 2 and in FIGS. 4 and 5.) Other embodiments of the invention substitute other types of fasteners, for example screws or bolts, for rivet 15 or 17. Thus, the present invention is not limited to any particular fastener.

Figure 2:
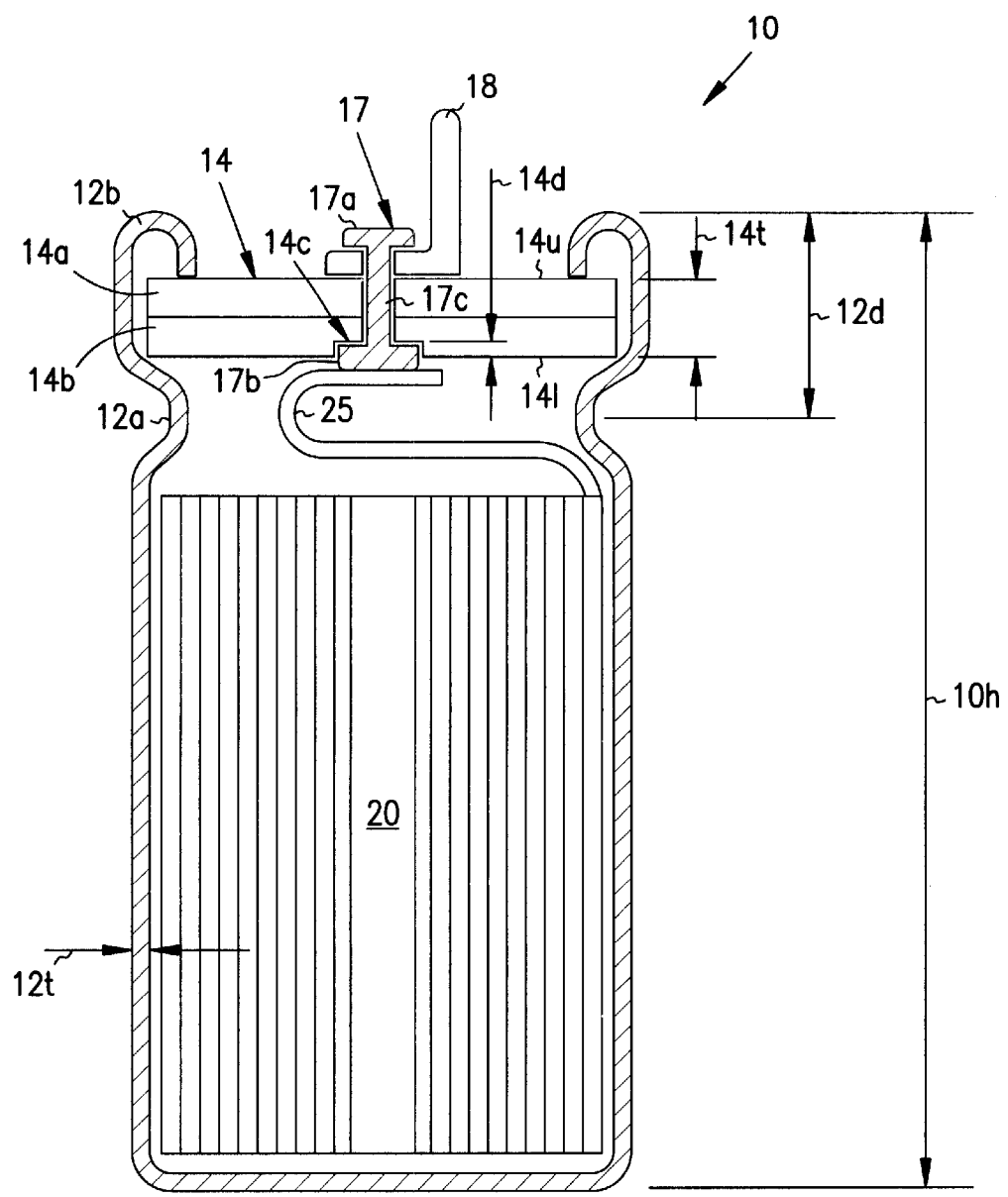

Aluminum case 12 includes a circumferential seating groove 12a and a rolled lip 12b which secure header assembly 14 within an otherwise open end of case 12. (In this exemplary embodiment, an aluminum plate fused or formed integrally with case 12 closes the opposite end, or bottom of case 12. However, in other embodiments it could be advantageous to close the bottom end with a second header assembly.) Seating groove 12a has an exemplary radius of about 0.035 inches. Lip 12b, which can be formed by rolling over the top edge of case 12, has an exemplary radius of about 0.015 inches. FIG. 2 also shows that seating groove 12a is a distance 12d, for example 0.145 inches, from rolled lip 12b.

FIG. 2, a cross-section taken along line 2—2 in FIG. 1, generally shows that case 12, which has a thickness 12t, houses an active element 20. Active element 20 conventionally comprises a rolled assembly of an anode foil, a cathode foil, and at least one insulative separator, with each foil connected respectively to one of lower rivet heads 15b and 17b via an aluminum foil tab, such as tab 25. Lower rivet heads 15b and 17b, in the exemplary embodiment, are ultrasonically welded to a respective aluminum foil tab, with the ultrasonics applied in a shear direction relative the tab and the rivet head. An exemplary technique uses a 40 Megahertz Ultrasonic Welder from Amtech Corporation with the following operating criteria:

| | |
|---|---|
| Energy: | 11–18 Joules |
| Clamp Force: | 13–18 pounds per square inch |
| Pressure: | 18–28 pounds per square inch |
| Amplitude: | 11–12 micrometers |
| Time Limit: | 0.15–0.50 seconds |
| Power: | 55–110 watts. |

However, other embodiments use different welders with different operating criteria.

FIG. 2 also shows that header assembly 14 comprises two bonded layers 14a and 14b, which provide a total header thickness 14t between upper and lower planar surfaces 14u and 14l. In the exemplary embodiment, header thickness 14t is about 2.5 millimeters, with layers 14a and 14b each being about 1.25 millimeters thick. Layer 14a consists of rubber and layer 14b consists of a phenolic resin. However, in other embodiments, header assembly 14 comprises three or more layers with a lesser or greater total thickness or one layer with an equal, lesser, or greater total thickness. Additionally, other embodiments form header assembly 14 from other materials: for example, thermoplastics, epoxies, and inert polymers using suitable molding technologies. Thus, header assembly 14 is not limited to any particular layered structure, dimensional selection, or composition.

Header assembly 14 also includes at least one recess 14c, which has a recess depth 14d less than the thickness of layer 14b in the exemplary embodiment, but more generally less than header thickness 14t. Recess 14c receives lower rivet head 17b, thereby reducing or preventing its extension below lower planar surface 14l. Recess depth 14d, in the exemplary embodiment, leaves the lower-most surface of lower rivet head 17b (or more generally fastener head 17b) lower than lower surface 14l of header assembly 14. However, in other embodiments of the invention, recess depth 14d allows the lower-most surface or portion of head 17b to be substantially flush, or coplanar, with lower surface 14l. Moreover, in yet other embodiments, recess depth 14d allows the lower-most surface or portion of head 17b to be above lower surface 14l. Thus, the invention is not limited to any particular recess depth 14d or recess profile. Likewise, the peripheral shape and size of recess 14c, though not visible in this view, are theoretically unlimited.

Figure 3:
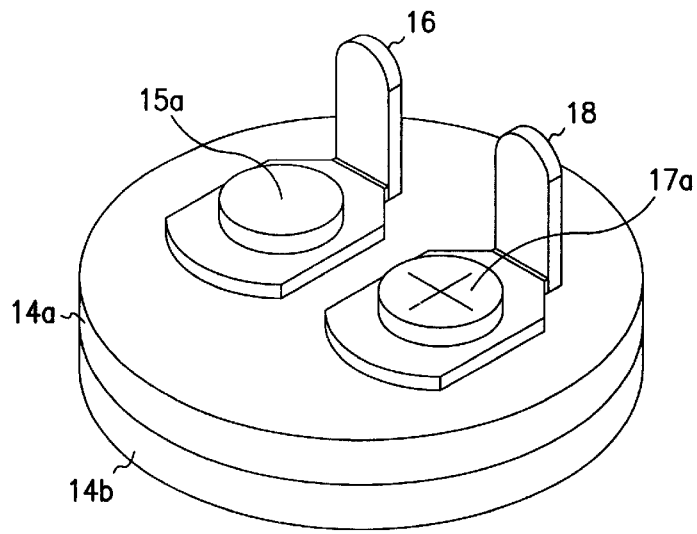
Figure 4:
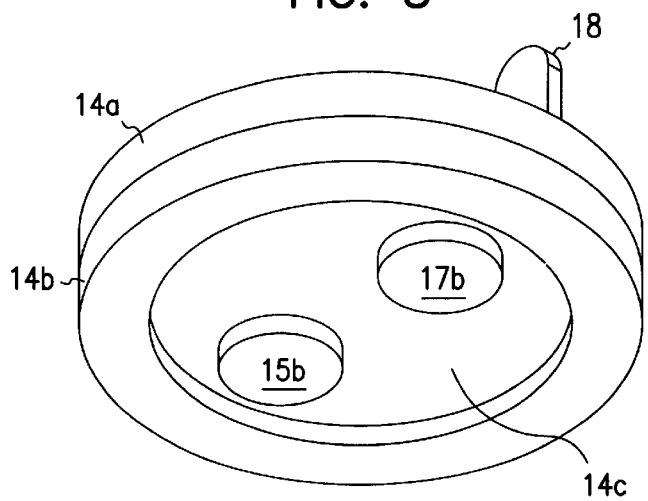
FIG. 4 is a bottom prospective view of header assembly 14, showing rivet heads 15b and 17b within a recess 14c.
Figure 5:
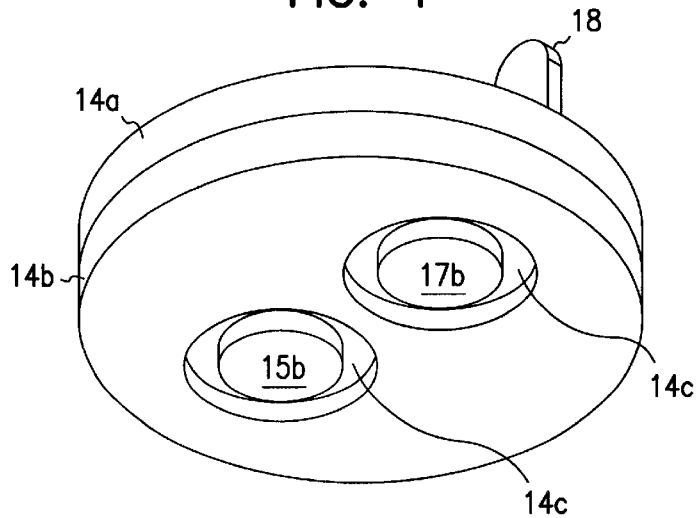
FIG. 5 is a prospective view of an alternative embodiment of header assembly 14, which provides two recesses 14c for rivet heads 15b and 17b.

FIGS. 3, 4, and 5 are perspective views, showing further aspects of header assembly 14 not clearly evident in FIGS. 1 and 2. In particular, FIG. 3 is a top perspective view of assembly 14, showing layers 14a and 14b, terminals 16 and 18, and upper rivet heads 15a and 17a. FIG. 4, a bottom perspective view of header assembly 14 based on FIG. 3, shows that layer 14b includes a single recess 14c which receives both of lower rivet heads 15b and 17b. FIG. 5, another bottom perspective view of assembly 14, shows two recesses 14c: one which receives lower rivet head 15b and another which receives lower rivet head 17b. Thus, a header assembly in accord with the present invention includes one or more recesses of any desirable shape and depth or combination of shapes and depths.

EXEMPLARY IMPLANTABLE DEFIBRILLATOR

Figure 6:
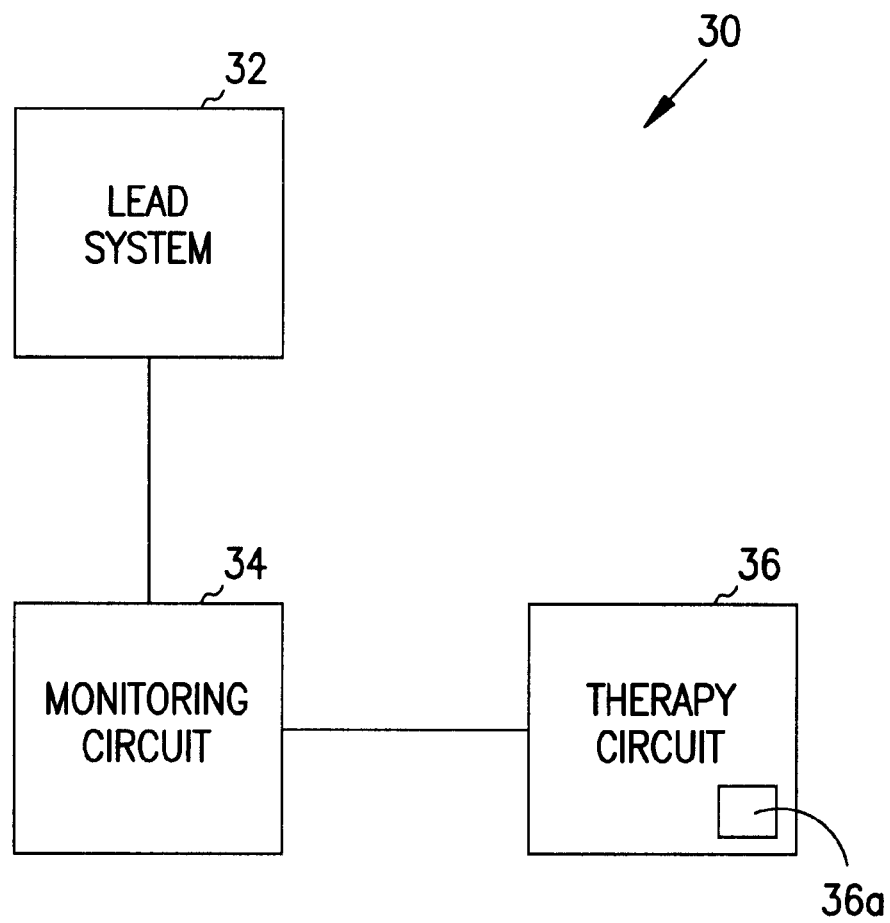
FIG. 6 is a block diagram of an implantable defibrillator 30 which includes one or more electrolytic capacitors 36a in accord with the invention.

FIG. 6 shows one of the many applications for space-saving electrolytic capacitor 10: a generic implantable defibrillator 30. Defibrillator 30 includes a lead system 32, which after implantation electrically contact strategic portions of a patient's heart, a monitoring circuit 34 for monitoring heart activity through one or more of the leads of lead system 32, and a therapy circuit 36 which incorporates one or more capacitors 36a similar to capacitor 10. Defibrillator 30 operates according to well known and understood principles.

In addition to implantable defibrillators and other cardiac rhythm management devices, such as pacemakers, the innovations of capacitor 10 can be incorporated into photographic flash equipment. Indeed, these innovations are pertinent to any application where small, high energy, low equivalent-series-resistance (ERS) capacitors are desirable.

CONCLUSION

In furtherance of the art, the inventors have devised a unique space-saving header for capacitors, particularly those for use in implantable defibrillators. In particular, the space-saving header includes at least one recess for mounting the head of a rivet flush (or more nearly flush) with the undersurface of the header, thereby allowing reduction in the height or volume of the capacitor and/or increases in the dimensions of other components, such as aluminum foils.

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

What is claimed is:

1. An implantable heart rhythm management device comprising: one or more leads for sensing electrical signals of a patient or for applying
   electrical energy to the patient; a monitoring circuit for monitoring heart activity of the patient through one
   or more of the leads; and a therapy circuit for delivering electrical energy through one or more of the
   leads to a heart of the patient, wherein the therapy circuit includes
   one or more aluminum electrolytic capacitors, each comprising:
     one or more terminals;
     a header having a header thickness and one or more recesses, with each recess having a depth less than the header thickness;
     one or more aluminum fasteners, with each fastener fastening one of the terminals to the header and having a head at least partially within one of the recesses; and
     an active element including one or more aluminum foils, with at least one of the foils electrically coupled to one of the aluminum fasteners.

2. The implantable heart rhythm management device of claim 1, wherein the header comprises first and second bonded layers, with the second bonded layer having a second thickness and with each recess having a depth less than the second thickness.

3. The implantable heart rhythm management device of claim 1, wherein the header comprises first and second bonded layers, with the first layer consisting essentially of rubber and the second layer consisting essentially of phenolic resin.

4. The implantable heart rhythm management device of claim 1, wherein the device is a defibrillator; one or more of the aluminum fasteners is a rivet; the active element includes one or more tabs coupled to one or more of the aluminum foils; and the rivet is ultrasonically welded to at least one of the tabs.

5. The implantable heart rhythm management device of claim 1, wherein each recess has a depth less than on e half the header thickness.

6. The implantable heart rhythm management device of claim 1, wherein each recess faces the active element.

7. An implantable heart rhythm management device comprising:
   one or more capacitors, with each capacitor comprising:
     a tubular housing having a longitudinal axis and having an opening defining a plane intersecting the longitudinal axis;
     a header filling or covering at least a portion of the opening, having a maximum thickness in a dimension parallel to the longitudinal axis, and having one or more recesses, each with a depth, measured in the dimension parallel to the longitudinal axis, which is less than the maximum thickness of the header; and
     one or more terminals fastened to the header with one or one or more fasteners, each fastener having a head at least partly within one of the recesses.

8. The implantable heart rhythm management device of claim 7, wherein each recess has a depth less than one half the header thickness.

9. The implantable heart rhythm management device of claim 7, wherein each capacitor further comprises an active element within the tubular housing and wherein each recess faces the active element.

10. The implantable heart rhythm management device of claim 7, wherein the housing and terminals consist essentially of aluminum.

11. An implantable heart rhythm management device comprising:
    one or more capacitors, with each capacitor comprising:
      a tubular housing having a longitudinal axis and having a closed end and an open end, each defining a plane intersecting the longitudinal axis;
      a header filling or covering at least a portion of the opening, having a maximum thickness in a dimension parallel to the longitudinal axis of the housing, and having one or more recesses, each with a depth, measured in the dimension parallel to the longitudinal axis, which is less than the maximum thickness of the header;
      an active element within the tubular housing between the closed end and the header, the active element including one or more conductive members; and
      one or more terminals fastened to the header with one or more conductive fasteners, each fastener having a head electrically coupled to one or more of the conducive members and at least partly within one of the recesses.

12. The implantable heart rhythm management device of claim 11, wherein each recess has a depth less than one half the maximum thickness of the header.

13. The implantable heart rhythm management device of claim 11, wherein each recess faces the active element.

14. An implantable heart rhythm management device comprising:
    one or more capacitors, with each capacitor including:
      capacitor casing means which defines an interior volume of the capacitor;
      header means having a header thickness attached to the capacitor casing means and having one or more each recess having a depth less than the header thickness; and
      terminating means fastened to the header with one or more fasteners, each fastener having a head at least partly within one of the one or more recesses.

* * * * *

UNITED STATES PATENT AND TRADEMARK OFFICE
CERTIFICATE OF CORRECTION

PATENT NO. : 6,385,490 B1  
DATED : May 7, 2002  
INVENTOR(S) : Michael J. O'Phelan, Robert R. Tong, Luke J. Christenson and Steven A. Rubin It is certified that error appears in the above-identified patent and that said Letters Patent is hereby corrected as shown below:

Title page,
Item [56], References Cited, OTHER PUBLICATIONS, insert -- , -- after "London", therefor.

Column 6,
Line 2, delete "on e" and insert -- one --, therefor.
Line 60, insert -- recesses, -- following "more", therefor.

Signed and Sealed this

Twenty-second Day of October, 2002

Attest:

Attesting Officer

JAMES E. ROGAN
Director of the United States Patent and Trademark Office